(12) United States Patent
Wu et al.

(10) Patent No.: US 11,376,292 B2
(45) Date of Patent: Jul. 5, 2022

(54) MICROBIAL FERMENTATION COMPOSITION SUBJECTED TO ENZYMOLYSIS, MICROBIAL FERMENTATION AND MICROBIAL TRANSFORMATION AND USE THEREOF

(71) Applicant: Bingxin WU, Shandong (CN)

(72) Inventors: Bingxin Wu, Shandong (CN); Xiaolin Sun, Shandong (CN); Jichen Lu, Shandong (CN); Xinhong Chu, Shandong (CN); Mei Lv, Shandong (CN)

(73) Assignee: Bingxin Wu, Shandong (CN)

( * ) Notice: Subject to any disclaimer, the term of this patent is extended or adjusted under 35 U.S.C. 154(b) by 132 days.

(21) Appl. No.: 16/630,477

(22) PCT Filed: Sep. 18, 2017

(86) PCT No.: PCT/CN2017/102122
§ 371 (c)(1),
(2) Date: Aug. 14, 2020

(87) PCT Pub. No.: WO2019/010813
PCT Pub. Date: Jan. 17, 2019

(65) Prior Publication Data
US 2021/0113636 A1    Apr. 22, 2021

(30) Foreign Application Priority Data
Jul. 13, 2017   (CN) .......................... 201710571073.X

(51) Int. Cl.
*A61K 36/07* (2006.01)
*A23L 33/105* (2016.01)
*A23L 33/16* (2016.01)
*A23L 33/135* (2016.01)
*A61K 33/04* (2006.01)
*A61K 33/30* (2006.01)
*A61K 35/745* (2015.01)
*A61K 35/747* (2015.01)
*A61K 36/258* (2006.01)

(52) U.S. Cl.
CPC ............ *A61K 36/07* (2013.01); *A23L 33/105* (2016.08); *A23L 33/135* (2016.08); *A23L 33/16* (2016.08); *A61K 33/04* (2013.01); *A61K 33/30* (2013.01); *A61K 35/745* (2013.01); *A61K 35/747* (2013.01); *A61K 36/258* (2013.01); *A61K 2236/15* (2013.01); *A61K 2236/19* (2013.01); *A61K 2236/37* (2013.01)

(58) Field of Classification Search
None
See application file for complete search history.

(56) References Cited

FOREIGN PATENT DOCUMENTS

| CN | 1237636 | * | 12/1999 |
| CN | 103356716 | * | 10/2013 |

* cited by examiner

*Primary Examiner* — Ralph J Gitomer
(74) *Attorney, Agent, or Firm* — JCIP Global Inc.

(57) ABSTRACT

A microbial fermentation composition subjected to enzymolysis, microbial fermentation and microbial transformation is prepared through extracting and hydrolyzing selected Edible and medicinal fungi *Agaricus blazei, Lentinus edodes, Flammulina velutipes* and *ginseng* of reinforcing vital energy, adding trace elements selenium, zinc and molybdenum, and fermenting and transforming by probiotics.

9 Claims, No Drawings

MICROBIAL FERMENTATION COMPOSITION SUBJECTED TO ENZYMOLYSIS, MICROBIAL FERMENTATION AND MICROBIAL TRANSFORMATION AND USE THEREOF

CROSS-REFERENCE TO RELATED APPLICATION

This application is a 371 of international application of PCT application serial no. PCT/CN2017/102122, filed on Sep. 18, 2017, which claims the priority benefit of China application no. 201710571073.X, filed on Jul. 13, 2017. The entirety of each of the above mentioned patent applications is hereby incorporated by reference herein and made a part of this specification.

BACKGROUND

Technical Field

The disclosure relates to a microbial fermentation composition and use thereof, in particular to an anti-cancer enzymatic composition subjected to microbial fermentation and transformation and use thereof.

Description of Related Art

Due to the stress from life and work as well as lack of exercise, nowadays people are in a sub-healthy state with low immunity, feel drowsy and get colds easily, and often experience gastrointestinal dysfunction. As the body is in the state of low immunity for a long time, the risk of cancer will increase.

Ginseng (Panax ginseng C.A. Meyer) is the root of perennial herb belonging to the genus Panax of the family Araliaceae, and is known as "king of herbs" as a traditional and precious Chinese medicine. Ginseng is widely used in nourishing health and medical treatment in China, Korea, Japan and even Asian countries. Modern pharmacological studies show that ginseng has pharmacological activities in the treatment and prevention of, for example, immunomodulation, anti-cancer, anti-ischemia, diabetes, atherosclerosis and anti-inflammatory.

Medicinal fungi refer to a class of fungi that can treat diseases and have medicinal value, that is, their mycelium, fruit bodies, sclerotia, or spores can produce amino acids, proteins, vitamins, polysaccharides, glycosides, alkaloids, and other substances, so they are fungi that can improve health or have the function of preventing, inhibiting or treating diseases. Some of these fungi not only can improve health but also can be eaten, and they are edible fungi as medicine and food. China has abundant resources for medicinal and edible fungi. According to rough estimation, about 2,500 types of such fungi have been recorded worldwide, and nearly 1,000 of them have been reported in China. Studies on the antitumor activity of edible and medicinal fungi mainly focus on the study of polysaccharides. Polysaccharides, proteins, nucleic acids, and lipids account for the four major components of life. In the past, people did not know much about the activity of polysaccharides, and thought that polysaccharides were only nutrients. After the 1960s, it was discovered that polysaccharides have multiple effects: it can control cell division, regulate cell growth and aging, can be used as an immune promoter, and has a therapeutic effect on tumors, cardiovascular diseases and hepatitis, so it has gained more attention since then. Polysaccharides has antitumor activity mainly because of the dextran with the main chain containing $\beta$-(1-3) or $\beta$-(1-4) and the side chain of $\beta$-(1-6). Studies show that the antitumor effect of dual-use fungal polysaccharides is performed through host mediating, which can activate T lymphocytes and improve organism's immune function. For example, Yunzhi polysaccharide can activate B cells, lentinan can restore T lymphocytes with decreased immune function, and Schizophyllan polysaccharide uses host reticuloendothelial cells to improve the host's non-specific defense function. These polysaccharides work on organisms with abnormal immune function. In vitro tests show that polysaccharides have no direct cytotoxic effect on the cells themselves.

SUMMARY

In order to solve the problems of low body immunity and reduced collective function, the present disclosure provides a microbial fermentation composition that can improve immunity and has anti-cancer effect.

The microbial fermentation composition of the present disclosure is prepared by selecting from the medicinal and edible fungi, including Agaricus blazei, Lentinus edodes, Flammulina velutipes and ginseng that can significantly increase energy, after being subjected to extraction and enzymolysis, trace elements such as selenium, zinc and molybdenum are added, and fermentation and transformation are carried out by using probiotics.

The weight g/volume mL percentage of the medicinal and edible fungi is: 1-3% of Agaricus blazei, 2-4% of Lentinus edodes, 1-4% of Flammulina velutipes; the weight g/volume mL percentage of the ginseng is 1-3%; the amount of the trace elements is: sodium selenite in an amount of 30-200 μg/100 mL, zinc sulfate heptahydrate 20-85 mg/100 mL, sodium molybdate dihydrate 50-150 μg/100 mL.

The probiotics are Bifidobacterium and Lactobacillus.

The preparation method of the microbial fermentation composition is as follows:

A. Extraction of fermentation substrate: Crush the dried ginseng, Agaricus blazei, Lentinus edodes, Flammulina velutipes, sieve them through a 65-80 mesh sieve, add drinking water that is 30 times the material weight and soak it in the water for 1 hour, heat and boil for 1.5 hours, and reduce the temperature to 90° C. Adjust and maintain the pH value between 5.5-7.0, add high temperature amylase, add an amount of 20 enzyme activity units×material weight/enzyme activity, maintain the temperature between 80-90° C., and stir the mixture evenly. End the amylase enzymolysis when the material solution and iodine solution no longer turn blue, reduce the temperature of the material solution to 50° C., adjust the pH of the material solution to 5.0-6.0, add pectin lyase in an amount of 0.1% volume of the material solution by volume/volume ratio, maintain the temperature at 45-50° C., carry out enzymolysis for 2 hours, end the enzymolysis and boil for 10 minutes. Inactivate the enzyme, filter, and take the supernatant, concentrate under reduced pressure until the concentration of Agaricus blazei, Lentinus edodes, Flammulina velutipes and ginseng reach the concentration to obtain fermentation substrate extract.

B. Ingredients and sterilization: add sodium selenite, zinc sulfate, sodium molybdate to the fermentation substrate extract, add 0.5% of glucose, 100 mg/100 mL of potassium dihydrogen phosphate, dipotassium hydrogen phosphate trihydrate 100 mg/100 mL, adjust pH value of the material solution, after being autoclaved, a fermentation substrate for subsequent microbial fermentation is obtained.

C. Inoculation and fermentation: Aseptically inoculate two cultures of pre-cultured *Bifidobacterium* genus into the sterile fermentation substrate obtained in step B, facultative anaerobic culture for 2 to 6 hours at 38±1° C., re-inoculate at least one culture of pre-cultured *Lactobacillus* and continue fermentation. When the pH of the fermentation broth drops to 4.1, reduce the temperature to 25° C. and maintained for another 24 hours, and end the fermentation.

D. Inactivation: Inactivate the fermentation broth that is completely fermented at 70° C. or 115° C. to obtain the microbial fermentation composition.

In the present disclosure, preferably, the weight g/volume mL percentage of the medicinal and edible fungi is: 2% of *Agaricus blazei*, 2% of *Lentinus edodes*, and 1% of *Flammulina velutipes*; the weight g/volume mL percentage of the *ginseng* is 2%.

In the present disclosure, preferably, the trace elements and the amount of the same are: sodium selenite in an amount of 70 μg/100 mL, zinc sulfate heptahydrate 50 mg/100 mL, sodium molybdate dihydrate 70 μg/100 mL.

Preferably, in step A of the preparation method, the process parameters in the enzymolysis process are: adjusting the pH to 6.0, adding a high-temperature amylase, maintaining the temperature at 85° C., and stirring uniformly; adjusting the pH of the material solution to 6.0, adding pectin lyase, maintaining the temperature at 45° C., hydrolyzing for 2 hours and ending the enzymolysis.

Preferably, in step B of the preparation method, the pH of the adjusted material solution is 7.0±0.1, and the autoclaving is performed at a temperature of 121° C. for 30 minutes.

Preferably, the *Bifidobacterium* genus described in step C of the preparation method refers to *Bifidobacterium bifidus*, *Bifidobacterium breve*, *Bifidobacterium adolescentis*, and *Bifidobacterium infantis*; the inoculation volume ratio of each strain is 0.6%, and the culture time is 6 hours. The *Lactobacillus* is *Lactobacillus acidophilus*, *Lactobacillus delbrueckii*, *Lactobacillus rhamnosus*, *Lactobacillus reuteri* or *Lactobacillus plantarum*; the inoculation volume ratio of each strain is 0.5%, and the fermentation temperature is 38±1° C.

Preferably, the inactivation temperature described in step D of the preparation method is 115° C., and the time is 10 minutes.

Preferably, the fermentation substrate extract described in step B of the preparation method is further added with sucrose with a weight mg/volume mL ratio of 3.0%, sucralose in an amount of 30 mg/100 mL and ferrous sulfate heptahydrate in an amount of 5.0 mg/100 mL.

Preferably, in step C of the preparation method, after the fermentation is completed, the oligoxylose syrup sterilized in advance at 115° C. for 40 minutes is added under sterile conditions, and the added amount is 1.5% by weight mg/volume mL ratio.

Another purpose of the present disclosure is to provide the use of the microbial fermentation composition in the preparation of a medicament or a health product for improving the immunity of the organism, preventing and treating tumors.

The main active ingredient of *ginseng* is ginsenosides, and now there are more than 50 kinds of monomeric saponins that have been separated with confirmed structure. Ginsenoside is a glycoside compound composed of aglycon connected with sugar, which belongs to triterpenoid saponin. Ginsenosides are divided into 3 types according to the structure of aglycones: diol-type ginsenosides (PPD), triol-type ginsenosides (PPT), and oleanolic-type ginsenosides. Both PPD and PPT ginsenosides are dammarane-type tetracyclic triterpenoids, which account for the majority of ginsenosides, and are currently considered to be one of the main active ingredients of *ginseng*. PPD-type saponins include, for example, ginsenosides Rb1, Rd, Rh2, etc., and PPT-type saponins include, for example, ginsenosides Re, Rg1, Rg2, etc., among which the content of ginsenosides Rb1, Rd, Re, etc. are higher, while the content of ginsenosides Rg3, Compound K, Rh2 are very rare and substantially do not exist in artificially cultivated *ginseng*, so it is a rare ginsenoside.

After oral administration of ginsenosides or *ginseng* extracts, ginsenosides are hydrolyzed to produce deglycosylated metabolites in an acidic gastric juice environment. In the intestine, glycoside hydrolases (such as β-glucosidase, a-rhamnoside, xylosidase, etc.) deglycosylation expressed by the intestinal flora can generate secondary metabolites or aglycones, which are absorbed into the systemic circulation by means of transmembrane transport, etc., and thus exert their efficacy. The differences between various ginsenosides are mainly the differences in the number and type of aglycones, glycosyl groups, and positions of glycosidic bonds. It has been proved that gastrointestinal metabolism position of saponins ingredients in traditional Chinese medicine is an important node that affects the absorption and efficacy of saponins ingredients. The glycoside hydrolase system expressed by the intestinal flora is the key factor in the node that mediates metabolism of saponin ingredients in the intestine.

*Flammulina velutipes* is beautiful in appearance and delicious, and has been widely used in medicated diets because of its various medicinal effects, also commonly known as edible and medicinal fungus and ornamental fungus. Studies have found that there are abundant anti-tumor active ingredients in *Flammulina velutipes*, including polysaccharides, flammulin, amycin, amycin protein and so on. Polysaccharide is one of the main active ingredients of *Flammulina velutipes*, and related functional evaluations have shown that polysaccharide has the function of improving immunity and anti-tumor effects. *Flammulina velutipes* contains flammulin, which is a special alkaline protein that can strengthen the defense function of organism's immune system, and has a significant inhibitory effect on cancer cells.

Lentinan can increase the activity of natural killer cells (NK cells) and the production of lymphokine-activated killer cells (LAK cells), which can activate cellular immune function and produce tumor necrosis factor. When combined with chemotherapy drugs, it can significantly improve the anti-tumor effect. Studies have shown that the level of biological activity of polysaccharides is related to its structure, and the introduction of chemical groups often enhances the activity of polysaccharides or makes polysaccharides generate new activities. Therefore, appropriate modification of polysaccharide structure is one of the focuses of the current research on polysaccharide.

*Agaricus blazei*, also known as Brazilian mushroom, is a precious and rare medicinal and edible fungus that is originated from Brazil and is rich in sugar and protein. Studies have shown that *Agaricus blazei* has the effects of regulating immunity, anti-tumor, anti-virus, anti-inflammatory, anti-fatigue and liver protection.

Trace element selenium, mainly presence in the form of selenium cysteine in protein, is a trace element necessary for human life activities and has a wide range of biological functions. A large number of studies have proven that selenium has anti-cancer and anti-cancer effects, and is a powerful inhibitor of breast cancer, liver cancer, skin cancer, colon cancer and gastric cancer, being capable of inhibiting adenogastric cancer and pregastric cancer of rats induced by carcinogen N-methyl-N'-nitro-N-nitrosoguanidine (MNNC), and preventing 3-methylcholanthrene (3-MCA) from inducing sarcomas of mice, thereby reducing the risk of sarcomas.

The trace element zinc is involved in the synthesis of metallothionein, thereby inhibiting the formation of free radicals. The zinc oxide can inhibit the destruction of single-strand DNA of human skin fibroblasts exposed to ultraviolet A1 radiation. Therefore, Zn may have a negative correlation with cancer.

Molybdenum is an essential micronutrient for animals and humans, which is a component of various enzymes that participates in and affects the metabolism of many substances in the body. Meanwhile, molybdenum has good prevention and treatment effects on pain, liver disease, cardiovascular and cerebrovascular disease as well as endemic diseases such as Keshan disease, dental caries, small cell hypochromic anemia, and regional hair loss.

The intestinal flora is an important "microecological organ" of the human body. As a living system symbiotic with the host, it participates in many physiological processes. The intestinal flora disorder is gradually considered to be an important pathological feature of certain metabolic diseases and mental diseases, and is closely related to the occurrence and development of such diseases. Intestinal flora disorders often aggravate the symptoms of the disease, and the disease process can adversely affect the intestinal flora and exacerbate the degree of intestinal flora. In addition, a variety of external factors can affect the homeostasis of the intestinal flora, such as stress, abuse of antibiotic, etc., which can often cause intestinal flora disorders. Systematic characterization of the composition and function of the intestinal flora is an important means for related research on the intestinal flora. Modern drug metabolism research shows that after many natural medicines are taken orally and enter the body, they come into contact with the microbial flora in the intestine, and bacteria metabolize and transform the drug to transform the precursor substance of the drug into the active ingredient of the drug to exert effect.

It is allegedly reported that lactic acid bacteria have anti-cancer effects, but the mechanism is not very clear. The possible mechanisms are: strengthening the organism's immune system; adjusting the intestinal flora to prevent the formation of carcinogens in the intestine; producing anti-mutagenic substances; degrading or adsorbing carcinogens, etc.

When the organism consumes too much greasy food, the fat increases in the body and metabolism increases as well. The cholate in liver is responsible for lipid metabolism by digesting fats through emulsification. When cholate passes through the intestine of the body and encounter pathogenic bacteria, carcinogens will be generated and cause bowel cancer. However, with the presence of probiotics, pathogenic bacteria will be suppressed, so the presence of cholate does not easily induce carcinogens. Scientists have also confirmed the above fact through experiments. Probiotic drinks can reduce the possibility of genetic damage to the intestinal cells in the body, thereby preventing certain cancers.

*Lactobacillus* is the main probiotic in the female reproductive tract. Heat-inactivated *Lactobacillus* has strong adhesion to cervical cancer cell strain HeLa cells. It has been confirmed that improving the immunogenicity of tumor cells and restoring the immune surveillance function of the tumor cells are important strategies for anti-tumor treatment. Studies conducted by Wang Hongyan et al. found that heat-inactivated *Lactobacillus* can indeed increase the immunogenicity of HeLa cells of the cervical cancer cell strain and activate the anti-tumor effects of T cells and NK cells, which provides new clues for probiotic-assisted tumor immunotherapy. Studies conducted by Chen Yutang et al. show that oral administration of probiotic for patients with liver cancer and liver cirrhosis during interventional treatment can effectively solve the intestinal flora imbalance of patients, and can reduce the risk of some liver cirrhosis complications in the short term without resulting significant functional impairment to liver.

Compared with the related art, the present disclosure selects probiotics for fermentation to transform inorganic trace elements such as selenium, zinc, molybdenum, etc. into organic trace elements, thereby reduces the accumulation toxicity and mutagenicity of inorganic trace elements, and improving the biological activity of trace elements. The selected medicinal and edible fungi and *ginseng* are rich in polysaccharides. After probiotic fermentation, the molecular weight of the above-mentioned fungi and *ginseng* is significantly reduced, which improves the tumor suppressing effect of fungal polysaccharide.

The formula of the fermentation composition contains *ginseng* extract, and the ginsenosides in the fermentation process are transformed into deglycosylation through metabolism of probiotics to generate secondary metabolites or aglycones, which are absorbed into the systemic circulation through transmembrane transport, etc. and then exert a medicinal effect. The difference between various ginsenosides lies mainly in aglycones. In the fermentation composition, the content of rare ginsenoside Rg3 increased significantly.

In experiments of vitro inhibition of HepGII cells (hepatocellular carcinoma cells) and Hela cells (cervical cancer cells) by the fermentation composition, it is shown that the fermentation composition subjected to probiotics fermentation had a significant inhibitory effect on tumor cell proliferation. As compared with the unfermented composition, the fermented composition has a significantly enhanced inhibitory effect on experimental tumor cells, and the difference is remarkable. In addition, the inhibitory effect of the fermentation composition on the tumor cells used in the test increases with the increase of the adopted concentration. The in vivo inhibitory effect of the fermentation composition on solid tumors of mouse S180 shows that the antitumor effect of the probiotic fermentation composition in high, medium and low doses is significantly improved. Although the related mechanism is not clear, the results of this study prove that no inhibitory effect on tumor cells was observed in the composition without probiotic transformation. Under the in vitro effect of intestinal beneficial flora, *ginseng*, *Agaricus blazei*, *Lentinus edodes*, or other fungal polysaccharides which are subjected to some known or unknown chemical modification or biological transformation or the probiotic bacteria themselves and their metabolites on tumor cells have higher inhibitory activity.

DESCRIPTION OF THE EMBODIMENTS

Example 1 Preparation of Probiotic Fermentation Composition A

Fermentation composition ingredients: The microbial fermentation composition includes the following ingredients: its weight/volume percentage is: *ginseng* 2.0%, *Agaricus blazei* 2.0%, *Lentinus edodes* 2.0%, *Flammulina velutipes* 1.0%, sodium selenite 70 μg/100 mL, zinc sulfate heptahydrate 50 mg/100 mL, sodium molybdate dihydrate 70 µg/100 mL. The preparation method is as follows.

a. Extraction of fermentation substrate: Crush the dried *ginseng, Agaricus blazei, Lentinus edodes, Flammulina velutipes*, sieve them through an 80 mesh sieve, add drinking water that is 30 times the material weight and soak it in the water for 1.0 hour, heat and boil for 1.5 hours, and reduce the temperature to 90° C. Adjust the pH to 6.0, add high-temperature amylase, add an amount of 20 enzyme activity units×material weight/enzyme activity, maintain the temperature at 85° C., and stir the mixture evenly. End the amylase enzymolysis when the material solution and iodine solution no longer turn blue, reduce the temperature of the material solution to 50° C., adjust the pH of the material solution to 6.0, add pectin lyase in an amount of 0.1% (volume of enzyme solution/volume of liquid), maintain the temperature at 45-50° C., carry out enzymolysis for 2 hours, end the enzymolysis and boil for 10 minutes. Inactivate the enzyme, filter, and take the supernatant, concentrate under reduced pressure until the desired volume is reached to obtain fermentation substrate extract.

b. Ingredients and sterilization: add sodium selenite in an amount of 70 µg/100 mL, zinc sulfate heptahydrate 50 mg/100 mL, sodium molybdate dihydrate 70 µg/100 mL, glucose in an amount of 0.5 g/100 mL, potassium dihydrogen phosphate in an amount of 100 mg/100 mL, dipotassium hydrogen phosphate trihydrate 100 mg/100 mL, sucrose in an amount of 3.0 g/100 mL, sucralose in an amount of 30 mg/100 mL, ferrous sulfate heptahydrate 5.0 mg/100 mL to the fermentation substrate extract, and adjust pH value of the material solution to 7.0±0.1, increase the autoclaving temperature to 121° C. and continues for 30 minutes, and the substrate for subsequent microbial fermentation is obtained.

c. Inoculation and fermentation: Aseptically inoculate two cultures of pre-cultured *Bifidobacterium bifidus* and *Bifidobacterium breve* into the sterile fermentation substrate of which the temperature is reduced to 40° C., and the inoculation amount is 0.6% (volume/volume). After performing facultative anaerobic culturing for 6 hours at 38±1° C., re-inoculate the cultures of pre-cultured *Lactobacillus acidophilus* and *Lactobacillus plantarum*, the inoculation amount is 0.5% (volume/volume), continue fermentation. When the pH of the fermentation liquid drops to 4.1, reduce the temperature to 25° C. and maintained for another 24 hours, and end the fermentation.

Formulation: Operate in aseptic condition, add sterilized oligoxylose syrup that is sterilized in advance at a temperature of 115° C. for 40 minutes, and the addition amount thereof is 1.5% of weight/volume ratio (mg/mL).

d. Inactivation: Inactivate the fermentation broth that is completely fermented at 115° C. for 10 minutes to obtain microbial fermentation composition A.

Example 2 Preparation of Probiotic Fermentation Composition B

Fermentation composition ingredients: The microbial fermentation composition includes the following ingredients: its weight/volume percentage is: *ginseng* 1.5%, *Agaricus blazei* 3.0%, *Lentinus edodes* 2.5%, *Flammulina velutipes* 2.0%, sodium selenite 100 µg/100 mL, zinc sulfate heptahydrate 30 mg/100 mL, sodium molybdate dihydrate 100 µg/100 mL.

a. Extraction of fermentation substrate: Crush the dried *ginseng, Agaricus blazei, Lentinus edodes, Flammulina velutipes*, sieve them through an 80 mesh sieve, add drinking water that is 30 times the material weight and soak it in the water for 1.0 hour, heat and boil for 1.5 hours, and reduce the temperature to 90° C. Adjust the pH to 6.0, add high-temperature amylase, add an amount of 20 enzyme activity units×material weight/enzyme activity, maintain the temperature at 85° C., and stir the mixture evenly. End the amylase enzymolysis when the material solution and iodine solution no longer turn blue, reduce the temperature of the material solution to 50° C., adjust the pH of the material solution to 6.0, add pectin lyase in an amount of 0.1% (volume of enzyme solution/volume of liquid), maintain the temperature at 45-50° C., carry out enzymolysis for 2 hours, end the enzymolysis and boil for 10 minutes. Inactivate the enzyme, filter, and take the supernatant, concentrate under reduced pressure until the desired volume is reached to obtain fermentation substrate extract.

b. Ingredients and sterilization: add sodium selenite in an amount of 100 µg/100 mL, zinc sulfate heptahydrate 30 mg/100 mL, sodium molybdate dihydrate 100 µg/100 mL, glucose in an amount of 0.5 g/100 mL, potassium dihydrogen phosphate in an amount of 100 mg/100 mL, dipotassium hydrogen phosphate trihydrate 100 mg/100 mL, sucrose in an amount of 3.0 g/100 mL, sucralose in an amount of 30 mg/100 mL, ferrous sulfate heptahydrate 5.0 mg/100 mL to the fermentation substrate extract, and adjust pH value of the material solution to 7.0±0.1, increase the autoclaving temperature to 121° C. and continues for 30 minutes, and the substrate for subsequent microbial fermentation is obtained.

c. Inoculation and fermentation: Aseptically insert two cultures of pre-cultured *Bifidobacterium infantis* and *Bifidobacterium adolescentis* into the sterile fermentation substrate of which the temperature is reduced to 40° C., and the inoculation amount is 0.6% (volume/volume). After performing facultative anaerobic culturing for 6 hours at 38±1° C., re-inoculate the cultures of pre-cultured *Lactobacillus rhamnosus* and *Lactobacillus reuteri*, the inoculation amount is 0.5% (volume/volume), continue fermentation. When the pH of the fermentation liquid drops to 4.1, reduce the temperature to 25° C. and maintained for another 24 hours, and end the fermentation.

d. Inactivation: Inactivate the fermentation broth that is completely fermented at 70° C. for 4 hours to obtain microbial fermentation composition B.

Experimental Example 1 In Vitro Test for Inhibiting Tumor Cell Proliferation Through a Microbial Fermentation Composition and an Unfermented Composition The microbial fermentation compositions A and B prepared in the examples were selected, and the composition A1 not subjected to microbial fermentation prepared through the ingredients in Example 1 is compared with the microbial fermentation composition A2 prepared through the ingredients in absence of *ginseng* in Example 1.

Take the cell strains HepGII and Hela, adjust the tumor cells respectively to $1\times10^4$ cells/L with the medium, and add 100 ul of cell suspension into each hole of a 96-hole plate and culture at 37° C. in the presence of 5% of $CO_2$ for a night. The next day, 10 ul, 20 ul, and 30 ul of different concentrations of the drug were added into each hole as test groups. Each group was set with 4-6 duplicate holes, and culture was continued at 37° C. in the presence of 5% of $CO_2$. After 24 hours of culture, add 10 ul of CCK8 reagent 1 hour before the experiment is terminated, continue to culture for 2 hours and then measure A450 mm absorbance. Therefore, calculate the cell growth inhibition rate. The experimental results are shown in Table 1.

TABLE 1

Inhibition rate of tumor cells by different compositions

| Groups | HepGII cell strain inhibition rate (%) | | | Hela cell strain inhibition rate (%) | | |
| --- | --- | --- | --- | --- | --- | --- |
| | 10 ul | 20 ul | 30 ul | 10 ul | 20 ul | 30 ul |
| 1 Unfermented composition A1 | 0 | 0 | 0 | 0 | 0 | 0 |
| 2 Fermented composition A2 free of ginseng | 11.0% | 37.2% | 69.3% | 2.73% | 40.3% | 60.2% |
| 3 Composition A | 17.6% | 53.4% | 85.4% | 3.0% | 48.4% | 90.1% |
| 4 Composition B | 13.1% | 45.6% | 71.1% | 3.40% | 37.6% | 69.5% |

Inhibition rate (%) = (absorbance value A of control group − absorbance value A of experimental group)/absorbance value A of control group × 100%

The experimental results show that, under the experimental conditions, the unfermented composition A1 of various concentration was not found to affect HepGII cell strains and Hela cell strains in terms of inhibitory effect. The microbial fermentation compositions A and B had an inhibitory effect on HepGII cell strains and Hela cell strains, and the inhibitory effect of composition A was stronger than that of composition B. Inhibition rate of *ginseng*-free fermentation composition A2 was significantly lower than that of composition A. Due to the fermentation and metabolism of probiotics, the molecular weight of the complex fungal polysaccharide is reduced, or the structure of ginsenosides is changed, or the probiotic bacteria itself and the metabolites product enhance the inhibitory effect on tumor cells, which makes the composition that initially has no inhibitory effect on HepGII cells strains and Hela cell strains in vitro have a stronger inhibitory effect.

Experimental Example 2 Comparison of Inhibitory Effect of Microbial Fermentation Composition and Unfermented Composition on Mouse Solid Tumors 1. Experimental samples: Fermented compositions A and B prepared in the examples, and unfermented compositions A1 and B1 of the same concentration were used for comparison.

Instrument: BP211D electronic analytical balance (Storis, Germany); inverted biological microscope LWD200-37T (Shanghai), syringes, stomacher, measuring tube, pipettes, etc.

Animals: 156 clean Kunming mice, weighing 18~22 g; purchased from Jinan Pengyue Experimental Animal Breeding Co., Ltd., license SCXK (Lu 2014-0007)

Grouping: 156 mice, randomly divided into 13 groups, 12 in each group. They are:

(1) physiological saline group, (2) fermentation composition A high-dose group, (3) fermentation composition A medium-dose group, (4) fermentation composition A low-dose group, (5) fermentation composition B high-dose group, (6) fermentation composition B medium-dose group, (7) fermented composition B low-dose group, (8) unfermented composition A1 high-dose group, (9) unfermented composition A1 medium-dose group, (10) unfermented composition A1 low-dose group, (11) unfermented composition B1 high-dose group (12) unfermented composition B1 medium-dose group, (13) unfermented composition B1 low-dose group Method:

5.1 Animal Modeling, Grouping and Administration

156 Kunming mice were placed in a ventilated and clean animal room at room temperature, they can eat and drink freely to adapt to the environment for 2 days. After routine disinfection, ascites fluid was extracted from S180 tumor mice, stained with trypan blue, and the number of viable cells was detected to reach 95% under a microscope. Thereafter, the tumor fluid was extracted and diluted with physiological saline until the number of tumor cell reaches $2 \times 10^7$/mL, 0.2 mL of which is administered to each mouse through right anterior axillary subcutaneous injection.

The mice were randomly divided into 13 groups after 24 hours following the inoculation. Animals in each group were subjected to intragastric administration for 15 consecutive days.

(1) The physiological saline group is the normal group, and the animals were given physiological saline on a daily basis after inoculation.

(2)(5)(8)(11) High-dose group: The high-dose group was administered with a dose converted at 20 times the recommended dose for human, each mouse was administered orally with 0.3 mL on a daily basis (concentrated by 2 times, equivalent to 0.6 mL of original composition).

(3)(6)(9)(12) Medium-dose group: The medium-dose group was administered with a dose converted at 10 times the recommended dose for human, each mouse was administered orally with 0.3 mL on a daily basis.

(4)(7)(10)(13) Low-dose group: The low-dose group was administered with a dose converted at 5 times the recommended dose for human, each mouse was administered orally with 0.3 mL on a daily basis (diluted by 1 time, equivalent to 0.15 mL of the original oral solution).

0.2 Determination of Tumor Inhibition Rate

Mice were sacrificed 14 days after administration, tumors were dissected out, tumor were weighed with an electronic balance, and tumor inhibition rates were calculated.

Tumor inhibition rate (%)=(mass of tumor in the model group−mass of tumor in the administration group)/mass of tumor in the model group× 100%

Results:

TABLE 2

Inhibitory effect of composition on solid tumors in mice ($\bar{X} \pm S$)

| | Groups | Dose (mL) | Number of animals | Weight of tumor | Tumor inhibition rate (%) |
|---|---|---|---|---|---|
| negative control | (1) physiological saline group | 0.3 | 12 | 2.44 ± 0.28 | 0 |
| fermentation composition A | (2) high-dose | 0.6 | 12 | 1.19 ± 0.12 | 51.23* |
| | (3) medium-dose | 0.3 | 12 | 1.31 ± 0.15 | 46.31* |
| | (4) low-dose | 0.15 | 12 | 1.54 ± 0.23 | 36.89* |
| unfermented composition A1 | (5) high-dose | 0.6 | 12 | 1.35 ± 0.17 | 44.67*# |
| | (6) medium-dose | 0.3 | 12 | 1.55 ± 0.24 | 36.48*# |
| | (7) low-dose | 0.15 | 12 | 1.83 ± 0.25 | 25.00*# |
| fermentation composition B | (8) high-dose | 0.6 | 12 | 1.24 ± 0.16 | 49.33* |
| | (9) medium-dose | 0.3 | 12 | 1.34 ± 0.21 | 45.11* |
| | (10) low-dose | 0.15 | 12 | 1.69 ± 0.20 | 30.69* |
| unfermented composition B1 | (11) high-dose | 0.6 | 12 | 1.45 ± 0.12 | 40.71*# |
| | (12) medium-dose | 0.3 | 12 | 1.68 ± 0.18 | 31.28*# |
| | (13) low-dose | 0.15 | 12 | 1.87 ± 0.23 | 23.16*# |

*Significantly different from the control group (P < 0.05)
Significant difference between fermented composition and unfermented composition at the same concentration (P < 0.05)

Compared with the negative control group, each experimental group has significant differences. In addition, compared with the same concentration of the unfermented composition, each group of the fermented composition with various dosage has significant differences. Probiotic fermentation transforms *ginseng*, Brazilian mushroom, *Flammulina velutipes*, and *Lentinus edodes*, which can improve the anti-tumor effect and reduce the effective concentration of the composition after fermentation.

Experimental Example 3 Determination of Rare Ginsenoside Rg3 Content in Microbial Fermentation Composition and Unfermented Composition Experiment sample: The fermentation composition A prepared in Example 1 was compared with the unfermented composition A1 at the same concentration as the control. Content of ginsenoside Rg3 in fermentation composition A2 of *ginseng* at the same concentration was also measured.

Experiment method: Measuring content of Rg3 in samples by high performance liquid chromatography. Measuring by high performance liquid chromatography (Appendix to the Chinese Pharmacopoeia)

Reagents and instruments: Ginsenoside Rg3 reference (provided by Nanjing Senberga Biotechnology Co., Ltd.); acetonitrile (chromatographically pure); methanol, n-butanol, ammonia (analytical pure).

Chromatographic conditions: Chromatographic column Beckman-ODS column (4.6 mm×250 mm, 5 μm), detection wavelength 203 nm, mobile phase: acetonitrile-0.05% phosphoric acid (50:50), flow rate 0.8 mL/min, column temperature 30° C.

Preparation of reference solution: Precisely weigh the appropriate amount of dried Rg3 reference and add methanol for dissolving to make a solution in a concentration of 40 μg per mL. The reference solution was obtained.

Preparation of test solution: Take test samples A, A1, A2, shake well, and accurately measure 25 mL, 100 mL were separated in the funnel. Water-saturated n-butanol was extracted three times, the n-butanol solution was combined, washed with 20 mL of ammonia test solution twice, and the n-butanol was evaporated to dryness in a water bath. The residue was dissolved in methanol and the volume was adjusted to 10 mL, shake well, filter through 0.45 μm membrane filtration. The test solution was obtained.

Measuring method: Precisely suck 10 μl of the reference solution and test solution each and inject them into the liquid chromatograph for measurement. The specific results are shown in Table 3.

TABLE 3

Content of rare ginsenoside Rg3 in the composition

| | Sample | Peak time | Peak area | Concentration μg/mL |
|---|---|---|---|---|
| 1 | Reference Rg3 | 11.784 | 2.669 | 40 |
| 2 | Unfermented composition A1 | Not detected | Not detected | — |
| 3 | Fermentation composition A2 only containing ginseng | 12.044 | 1.671 | 10 |
| 4 | Fermentation composition A | 11.970 | 3.853 | 23 |

It can be seen from the experimental results that ginsenoside Rg3 was not detected in the unfermented composition, and the fermentation composition after detection was found to have the content of ginsenoside Rg3 in a concentration of 23 μg/mL, and the fermentation composition A2 containing the same concentration *ginseng* only had ginsenoside Rg3 in a concentration of 10 μg/mL. It is assumed that Brazilian mushroom (*Agaricus blazei*), *Lentinus edodes*, and *Flammulina velutipes* may have an effect on the growth of probiotics or the activity of glycosidase, so that in the composition of the present disclosure, the metabolic conversion ability of probiotics to ginsenoside is improved, and higher concentrations of rare ginsenoside Rg3 are produced in the fermented composition prepared by this method. Ginsenoside has obvious physiological activity and is also the most effective medicinal ingredient in *ginseng* ingredients. At present, about 50 kinds of ginsenoside ingredients have been separated from *ginseng*. Pharmacological studies show that ginsenosides generally have pharmacological effects such as anti-tumor, antioxidant, memory improvement, anti-fatigue, and nerve protection. Ginsenoside Rg3 was initially separated from red *ginseng*, and it mainly acts in the G2/M phase of the cell proliferation cycle. Ginsenoside Rg3 can induce tumor cell apoptosis, selectively inhibit tumor cell adhesion and infiltration, inhibit tumor neovascularization, and enhance immunity of organism, etc. However, the natural content of these saponins is very low, for example, the content of Rg3 in white *ginseng* is only 0.0003%. Through the method of the present disclosure, the content of rare ginsenoside Rg3 in the composition can be significantly increased.

What is claimed is:

1. A microbial fermentation composition, is prepared through extracting and hydrolyzing medicinal and edible fungi *Agaricus blazei, Lentinus edodes, Flammulina velutipes* and *ginseng*, adding trace elements selenium, zinc and molybdenum, and fermenting and transforming by probiotics:
   a weight g/volume mL percentage of the medicinal and edible fungi is: 1-3% of *Agaricus blazei*, 2-4% of *Lentinus edodes*, 1-4% of *Flammulina velutipes*; a weight g/volume mL percentage of the *ginseng* is 1-3%; an amount of the trace elements is: 30-200 µg/100 mL of sodium selenite, 20-85 mg/100 mL of zinc sulfate heptahydrate, and 50-150 µg/100 mL of sodium molybdate dihydrate;
   wherein the probiotics are *Bifidobacterium* and *Lactobacillus*;
   wherein a preparation method of the microbial fermentation composition is as follows:
   A. extraction of fermentation substrate: crushing dried *ginseng, Agaricus blazei, Lentinus edodes, Flammulina velutipes*, sieving through a 65-80 mesh sieve, adding drinking water that is 30 times the material weight and soaking for 1 hour, heating and boiling for 1.5 hours, and when reducing temperature to 90° C., adjusting a pH value between 5.5-7.0, adding high temperature amylase, adding an amount of 20 enzyme activity units×material weight/enzyme activity, maintaining the temperature between 80-90° C., and stirring evenly, ending amylase enzymolysis when material solution and iodine solution no longer turn blue, reducing the temperature of the material solution to 50° C., adjusting a pH value of the material solution to 5.0-6.0, adding pectin lyase, adding an amount of 0.1% volume of the material solution by volume/volume ratio, maintaining the temperature at 45-50° C., enzymolyzing for 2 hours, ending the enzymolyzing and boiling for 10 minutes, inactivating enzyme, filtering, and taking supernatant, concentrating under reduced pressure until concentration of *Agaricus blazei, Lentinus edodes, Flammulina velutipes* and *ginseng* reaches the concentration to obtain a fermentation substrate extract;
   B. ingredients and sterilization: adding sodium selenite, zinc sulfate, sodium molybdate to the fermentation substrate extract, adding 0.5% of glucose, 100 mg/100 mL of potassium dihydrogen phosphate, 100 mg/100 mL of dipotassium hydrogen phosphate trihydrate, adjusting the pH value of the material solution, after autoclaving, a fermentation substrate for subsequent microbial fermentation is obtained;
   C. inoculation and fermentation: aseptically inoculating two cultures of pre-cultured *Bifidobacterium* genus into the sterile fermentation substrate obtained in step B, facultative anaerobic culture at 38±1° C. for 2 to 6 hours, inoculating at least one culture of pre-cultured *Lactobacillus* and continuing fermentation, when a pH value of a fermentation broth drops to 4.1, reducing the temperature to 25° C. and maintaining for another 24 hours, and ending the fermentation;
   D. inactivation: inactivating the fermentation broth that is completely fermented at 70° C. or 115° C. to obtain the microbial fermentation composition.

2. The microbial fermentation composition according to claim 1, wherein the weight/volume percentage of each ingredient in the microbial fermentation composition is: 2% of *ginseng*, 2% of *Agaricus blazei*, 2% of *Lentinus edodes*, and 1% of *Flammulina velutipes*.

3. The microbial fermentation composition according to claim 1, wherein the trace elements and the amount thereof are: 70 µg/100 mL of sodium selenite, 50 mg/100 mL of zinc sulfate heptahydrate, and 70 µg/100 mL of sodium molybdate dihydrate.

4. The microbial fermentation composition according to claim 1, wherein process parameters in the enzymolysis process in step A of the preparation method are: adjusting the pH value to 6.0, adding the high temperature amylase, maintaining the temperature at 85° C., and stirring evenly; adjusting the pH value of the material solution to 6.0, adding pectin lyase, maintaining the temperature at 45° C., enzymolyzing for 2 hours and ending the enzymolyzing.

5. The microbial fermentation composition according to claim 1, wherein in step B of the preparation method, the pH value of the adjusted material solution is 7.0±0.1, and the autoclaving is performed at temperature of 121° C. and time of 30 minutes.

6. The microbial fermentation composition according to claim 1, wherein the *Bifidobacterium* genus described in step C of the preparation method refers to *Bifidobacterium bifidus, Bifidobacterium breve, Bifidobacterium adolescentis*, and *Bifidobacterium infantis*, an inoculation volume ratio of each strain is 0.6%, and culture time is 6 hours; the *Lactobacillus* is *Lactobacillus acidophilus, Lactobacillus delbrueckii, Lactobacillus rhamnosus, Lactobacillus reuteri* or *Lactobacillus plantarum*, an inoculation volume ratio of each strain is 0.5%, and fermentation temperature is 38±1° C.

7. The microbial fermentation composition according to claim 1, wherein an inactivation temperature described in step D of the preparation method is 115° C., and an inactivation time is 10 minutes.

8. The microbial fermentation composition according to claim 1, wherein the fermentation substrate extract described in step B of the preparation method is further added with sucrose with a weight mg/volume mL ratio of 3.0%, 30 mg/100 mL of sucralose and 5.0 mg/100 mL of ferrous sulfate heptahydrate.

9. The microbial fermentation composition according to claim 1, wherein in step C of the preparation method, after the fermentation is completed, an oligoxylose syrup sterilized at 115° C. for 40 minutes is added under sterile conditions, and an added amount is 1.5% by weight mg/volume mL ratio.

* * * * *